United States Patent [19]

Krzysik

[11] Patent Number: 5,288,482

[45] Date of Patent: Feb. 22, 1994

[54] SILICONE CONTAINING LIP CARE COSMETIC COMPOSITION

[75] Inventor: Duane G. Krzysik, Midland, Mich.

[73] Assignee: Dow Corning Corporation, Midland, Mich.

[21] Appl. No.: 29,503

[22] Filed: Mar. 11, 1993

[51] Int. Cl.$^5$ .......................................... A61K 7/027
[52] U.S. Cl. ...................................... 424/64; 424/63; 424/401; 424/DIG. 5; 514/772.3; 514/949
[58] Field of Search ............. 424/63, 64, 401, DIG. 5; 514/772.3, 949

[56] References Cited

U.S. PATENT DOCUMENTS 4,425,364  1/1984  Vanlerberghe et al. ............. 424/358
5,216,033  6/1993  Preira et al. ........................ 514/844

FOREIGN PATENT DOCUMENTS 2-64510  3/1990  Japan ............................. A61K 7/00

*Primary Examiner*—Thurman K. Page
*Assistant Examiner*—Jyothsna Venkat
*Attorney, Agent, or Firm*—James L. DeCesare

[57] ABSTRACT

A lipcare cosmetic composition containing as ingredients an emollient including castor oil, a wax, a suspending agent, a coloring agent, and as an additional ingredient, an organosilicon compound. The improvement resides in increasing the durability of lipcare products by including an alkylmethylpolysiloxane having the formula

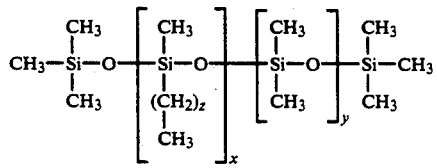

in which x has a value of 1–300; y has a value of 1–50; and z has a value of 5–50.

16 Claims, No Drawings

SILICONE CONTAINING LIP CARE COSMETIC COMPOSITION

BACKGROUND OF THE INVENTION

This invention is directed to personal care products, and more particularly to a cosmetic composition in the form of a lip care preparation containing certain alkylmethylsilicone copolymers. Inclusion of these alkylmethylsilicone copolymers in compositions formulated for the care of the lips has been found to contribute to the durability, and hence the increased wearability of lip products.

Lipstick is one of the most widely used decorative cosmetic preparations. The primary duties of lip care preparations including lipsticks are to prevent the drying and cracking of the lips, to impart color to pale lips, to alter the shape of the lips, and to match lip color with the color of hair, accessories, or clothing. Its handy form enables a female to renew her make-up repeatedly throughout the day, and to achieve a fresh look, or to add a protective coating.

Consumers expect a lip care product which can be applied effortlessly, which produces an even coating on the lips of a desired thickness, and which possesses a reasonable amount of durability and life expectancy.

Such lip care products run the gamut from a lip fix which is used as a base before applying a color lipstick, a lip gloss which is applied last and provides the lips with a strong stylish sheen, to a lip contour pencil which frames the lips with a line. Because many lip care products include color, staining of various items which come into contact with the lips is always a potential and otherwise undesirable feature. Therefore, whatever the form of the lip care product, durability is one of the important expectations of a successful over the counter cosmetic lip care product.

The alkylmethylsilicone copolymers of the present invention have been found to meet this need for increased durability of lip care cosmetics.

SUMMARY OF THE INVENTION

The present invention relates to color cosmetics sticks such as lipsticks, cover make-up sticks, and eyeshadow pencils, which color cosmetic sticks have been found to be harder to remove from the skin and lips by rubbing. The stick products exhibit improved wearability, substantivity, and durability, because of the presence in the stick product of certain alkylmethylsilicone copolymers. The copolymer as an essential ingredient in the stick product functions to increase the wear time of the stick product, and prevents transfer of the cosmetic in comparison to cosmetic products which do not contain the copolymer. In addition, the cosmetic stick products of the present invention have been observed to exhibit the added benefits of improved gloss of the stick itself, and improved gloss of the cosmetic on the skin and lips, because of the presence in the cosmetic stick product of the alkylmethylsilicone copolymer.

These and other features, objects, and advantages, of the herein defined present invention will become more apparent from a consideration of the following detailed description thereof.

DETAILED DESCRIPTION OF THE INVENTION

In accordance with the present invention, lip care cosmetic compositions may be formulated containing a variety of ingredients. However, the essential ingredients include one or more emollients including castor oil, one or more waxes, a suspending agent, one or more coloring agents or materials, and the durability enhancing alkylmethylsilicone copolymer.

In addition, it may be desirable to include other materials such as sunscreen agents; vitamins such as Vitamin A, Vitamin B, Vitamin D, Vitamin E, ascorbic acid, and biotin; hormones; amino acids; antioxidants such as propyl, octyl, and dodecyl esters of gallic acid, butylated hydroxytoluene, butylated hydroxyanisole (BHA), and natural mixed tocopherols; opacifiers such as titanium dioxide and fatty alcohols; surfactants, pH modifiers, preservatives, fragrances, and humectants.

Waxes which may be employed include carnauba, beeswax, ceresin, paraffin, candelilla, bayberry, montan, spermaceti, castor wax, ozokerite, microcrystalline waxes, and Fisher-Tropsch waxes.

Colorants include any of the U.S. government Food and Drug Administration (FDA) certified inorganic and organic dyes and lakes such as carmine, iron oxide, mica, titanium dioxide, ultramarines, zinc oxide, bismuth oxychloride; and D & C Blue No. 1, D & C Orange No. 5, D & C Red No. 6 Aluminum Lake, D & C Red No. 7 Calcium Lake, D & C Green No. 8, D & C Red No. 17, FD & C Blue No. 1, FD & C Red No. 3, FD & C Yellow No. 6, External D & C Violet No. 2, which are the CTFA adopted names of The Cosmetic, Toiletry, and Fragrance Association, Washington, D.C.

Preservatives which may be used are methyl paraben, propyl paraben, butyl paraben, Quaternium-15, diazolidinyl urea, imidazolidinyl urea, and mixtures thereof.

Among the numerous humectants which may be employed are polyhydroxy alcohols such as sorbitol, glycerin, propylene glycol, and hexanetriol; sugar and starch derivatives such as alkoxylated glucose, and hydrolyzed mucopolysaccharides; D-panthenol, hyaluronic acid, lactamide monoethanolamine, acetamide monoethanolamine, urea, guanidine, glycolic acid and glycolate salts, lactic acid and lactate salts; and mixtures thereof.

Emollient oils which can be employed in the present invention include mineral oil, peanut oil, sesame oil, avocado oil, coconut oil, cocoa butter, almond oil, safflower oil, corn oil, cotton seed oil, castor oil, olive oil, jojoba oil, paraffin oil, cod liver oil, palm oil, soybean oil, wheat germ oil, linseed oil, and sunflower seed oil; fatty acid esters such as isopropyl myristate, isopropyl palmitate, isopropyl stearate, butyl stearate, cetyl stearate, diisopropyl adipate, isodecyl oleate, diisopropyl sebacate, and lauryl lactate; fatty acids such as lauric, myristic, palmitic, stearic, oleic, linoleic, and behenic, acid; fatty alcohols such as lauryl, myristyl, cetyl, stearyl, isostearyl, oleyl, ricinoleyl, erucyl, and 2-octyl dodecanol, alcohol; lanolin and its derivatives such as lanolin, lanolin oil, lanolin wax, lanolin alcohols, lanolin fatty acids, isopropyl lanolate, ethoxylated lanolin, and acetylated lanolin alcohols such as ACETULAN ®, a trademark and product of Amerchol Corporation, Edison, N.J.; hydrocarbons such as petrolatum and squalane; and silicones such as non-volatile siloxane fluids and volatile siloxane fluids.

Sunscreen agents may be included in some instances, and can be used in amounts which are within the restricted limits or less as established by the U.S. government Food and Drug Administration (FDA). Representative sunscreen agents or mixtures of such agents which may be used in the preparation of the compositions of the present invention include 4-aminobenzoic acid; homomethyl salicylate; 2-hydroxy-4-methoxy benzophenone; 2-phenylbenzimidazol-5-sulfonic acid; 4-dimethylamino benzoic acid 2-ethylhexyl ester; 4-methoxy cinnamic acid isoamyl ester; 4-methoxy cinnamic acid 2-ethylhexyl ester; 3-(4'-methyl) benzylidene-bornane-2-one; 1-(4'-isopropylphenyl)-3-phenyl-1-propane-1,3-dione; and 1-(4'-t-butylphenyl)-3-(4-methoxyphenyl)propane-1,3-dione.

Fragrances which may be used include natural products such as ambergris, benzoin, civet, clove, leaf oil, jasmine, mate', mimosa, musk, myrrh, orris, sandalwood oil and vetivert oil; aroma chemicals such as amyl salicylate, amyl cinnamic aldehyde, benzyl acetate, citronellol, coumarin, geraniol, isobornyl acetate, ambrette, and terpinyl acetate; and the various classic family perfume oils such as the floral bouquet family, the oriental family, the chypre family, the woody family, the citrus family, the canoe family, the leather family, the spice family, and the herbal family.

Suspending agents which may be used include polyacrylates, sodium alignate, gum arabic, guar gum, carboxyvinyl polymers, cellulose derivatives such as methylcellulose, ethyl cellulose, methylhydroxypropylcellulose, hydroxypropylcellulose, carboxymethylcellulose, and polypropylhydroxyethylcellulose; starch and starch derivatives such as hydroxyethylamylose, and starch amylose; polyvinyl alcohol, locust bean gum, vegetable gums, magnesium aluminum silicate such as Veegum, a tradename of R. T. Vanderbilt Company, Incorporated, Norwalk, Conn.; saccharide and saccharide derivatives such as fructose, glucose, and PEG-120 methyl glucose dioleate; and the various organically modified montmorillonite clays sold under the trademark BENTONE ® by Rheox Incorporated, Highstown, N.J., such as BENTONE ® 38.

As noted above, the durability enhancement improvement according to the present invention resides in the use as an ingredient of the lip care composition, of an alkylmethylsilicone copolymer. The alkylmethylsilicone copolymer that is used for providing the enhancement of durability has the formula:

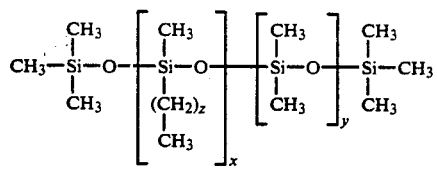

in which x has a value of 1–50; y has a value of 1–300; and z has a value of 5–50. Preferably, x has a range of 3–40; y has a range of 2–190; and z has a range of 5–30.

Methods for the preparation of such materials are known in the art, and such methods are described in, for example, U.S. Pat. No. 5,017,221 which issued May 21, 1991, and U.S. Pat. No. 5,160,494 which issued Nov. 3, 1992, both of which are incorporated herein by reference. Basically, such methods involve the reaction of a linear siloxane having SiH functionality in the chain with a cyclic siloxane containing $Me_2SiO$ units, and contacting the reaction product with a slight stoichiometric excess of an alkene in the presence of a platinum on carbon catalyst.

The invention will be further illustrated by reference to the following examples in which a number of lipstick compositions were formulated.

EXAMPLE I

In Table I, various ingredients which were used to formulate lipsticks are shown in amounts expressed as percent by weight. Each lipstick was prepared by mixing and heating together the various ingredients shown in the tables in the amounts indicated, until a uniform mixture was obtained. The mixture was cooled to seventy degrees Centigrade and poured into a mold of a lipstick shaft. After one minute, the mold was placed in a water bath at eighteen degrees Centigrade until a solid stick was formed. The lipstick was tested for durability in accordance with Example II. The pigment employed in Example I for the preparation of the lipstick was in the form of a pigment grind which was a mixture of coloring agents containing thirty percent by weight of titanium dioxide, thirty percent by weight of D & C Red No. 6 Aluminum Lake, and forty percent by weight of D & C Red No. 7 Calcium Lake. The pigment was added to the lipstick as a dispersion in castor oil containing seven percent by weight pigment and twenty-three percent by weight castor oil.

Lipstick "A" containing no alkylmethylsilicone copolymer was used as a control. For comparative purposes, there was also lipsticks E and F containing "Other Silicones" which were a phenyltrimethylsiloxane fluid, and a soft solid mixture of stearyl alcohol and trimethylsiloxy stearate of the formula $CH_3(CH_2)_{16}CH_2OSi(CH_3)_3$.

EXAMPLE II

Each of the lipsticks "A–H" and "J" shown in Table I were tested for durability by volunteers. The volunteers applied the lipstick to the skin and attempted to remove the lipstick by rubbing the area with a soft tissue, or with mild rubbing using IVORY ® soap and water. Each lipstick was evaluated on the basis of ease of removal. It was determined that in all cases, the lipsticks B–D, G, H, and J, which contained the alkylmethylsilicone copolymer, were harder to remove than the control lipstick "A" and the comparative sticks E and F, and hence were more durable. The alkylmethylsilicone copolymer used in each lipstick formulation in Table I is shown in Table I by reference to the above formula. Thus, Table I identifies the value for the integers "x" and "y" of the two difunctional repeating units of the copolymer. The "z" value is expressed in terms of the total number of carbon atoms in the long chain alkyl group in the difunctional repeating unit "x".

The suspending agent shown in Table I is an organically modified montmorillonite clay sold under the trademark BENTONE ® 38 by Rheox Incorporated, Highstown, N.J. The emollient ACETULAN ® is an acetylated lanolin alcohol, and a trademark and product of Amerchol Corporation, Edison, N.J.

TABLE I

| INGREDIENTS | LIPSTICK FORMULATIONS (Weight percent) | | | | | | | | |
| --- | --- | --- | --- | --- | --- | --- | --- | --- | --- |
|  | A | B | C | D | E | F | G | H | J |
| Octyl dodecanol | 10.00 | 10.00 | 10.00 | 10.00 | 10.00 | 10.00 | 10.00 | 10.00 | 10.00 |

TABLE I-continued

| INGREDIENTS | LIPSTICK FORMULATIONS (Weight percent) | | | | | | | | |
|---|---|---|---|---|---|---|---|---|---|
| | A | B | C | D | E | F | G | H | J |
| Candelilla Wax | 7.00 | 7.00 | 7.00 | 7.00 | 7.00 | 7.00 | 7.00 | 7.00 | 7.00 |
| Ozokerite Wax | 4.00 | 4.00 | 4.00 | 4.00 | 4.00 | 4.00 | 4.00 | 4.00 | — |
| Carnauba Wax | 2.50 | 2.50 | 2.50 | 2.50 | 2.50 | 2.50 | 2.50 | 2.50 | 2.50 |
| Lanolin Oil | 15.00 | — | — | — | — | — | 10.00 | 10.00 | 14.00 |
| ACETULAN ® | 2.50 | 2.50 | 2.50 | 2.50 | 2.50 | 2.50 | 2.50 | 2.50 | 2.50 |
| BENTONE ® 38 | 0.60 | 0.60 | 0.60 | 0.60 | 0.60 | 0.60 | 0.60 | 0.60 | 0.60 |
| Propyl paraben | 0.10 | 0.10 | 0.10 | 0.10 | 0.10 | 0.10 | 0.10 | 0.10 | 0.10 |
| Butylated hydroxyanisole | 0.05 | 0.05 | 0.05 | 0.05 | 0.05 | 0.05 | 0.05 | 0.05 | 0.05 |
| Castol Oil | 28.25 | 28.25 | 28.25 | 28.25 | 28.25 | 28.25 | 28.25 | 28.25 | 28.25 |
| Pigment Grind | 30.00 | 30.00 | 30.00 | 30.00 | 30.00 | 30.00 | 30.00 | 30.00 | 30.00 |
| a. Pigment 7% | | | | | | | | | |
| b. Castor Oil 23% | | | | | | | | | |
| Silicone Copolymer | | | | | | | | | |
| A. $C_{12}$ x = 6 y = 3 | — | 15.00 | — | — | — | — | — | — | — |
| B. $C_{16}$ x = 6 y = 3 | — | — | 15.00 | — | — | — | — | — | — |
| C. $C_{18}$ x = 5 y = 95 | — | — | — | 15.00 | — | — | — | — | — |
| D. $C_{18}$ x = 6 y = 3 | — | — | — | — | — | — | 5.00 | — | — |
| E. $C_{24-28}$ x = 6 y = 3 | — | — | — | — | — | — | — | 5.00 | — |
| F. $C_{30}$ x = 6 y = 3 | — | — | — | — | — | — | — | — | 5.00 |
| Other Silicones | | | | | | | | | |
| A. Trimethyl-siloxystearate | — | — | — | — | 15.00 | — | — | — | — |
| B. Polyphenyl-methylsiloxane | — | — | — | — | — | 15.00 | — | — | — |

Lipstick products in accordance with the present invention contain from zero to twenty-five percent by weight of one or more emollients, preferably at least one percent and more preferably ten to fifteen percent by weight; ten to twenty percent by weight of one or more waxes, preferably fifteen percent by weight; 0.5 to 1.0 percent by weight of a suspending agent which functions primarily to suspend the pigments; three to ten percent by weight of one or more coloring agents; forty to sixty percent by weight of castor oil; one to twenty percent by weight of the alkylmethylsilicone copolymer of the invention; 0.1 to 0.5 percent by weight of a preservative; and 0.05 to 0.1 percent by weight of an antioxidant.

Because of the presence in the molecule of at least two distinct repeating difunctional units, the copolymeric alkylmethylsilicones of this invention possess a high molecular weight; in comparison to polymeric silicones containing only one difunctional repeating unit of the type described for example in Japanese Kokai Patent Application 3264510 published Nov. 25, 1991. Because of this higher molecular weight, durability is provided as a property of the copolymer, rendering lipcare products containing the copolymeric form of the alkylmethylsilicones difficult to remove by rubbing.

Thus, the difunctional dimethylsiloxane repeating unit —[(CH$_3$)$_2$SiO]$_y$— provides waterproofing to the skin, and the difunctional alkylmethylsiloxane repeating unit —[CH$_3$(CH$_2$)$_z$CH$_3$SiO]$_x$ provides an organic skin compatible nature to the copolymer. The presence in the molecule of the combination of these two repeating units renders the copolymer skin compatible, therefore durable and difficult to wash off. This is a significant advantage over the polymers of the Kokai 3264510 patent. Further, some of the polymers of the Kokai 3264510 patent are volatile materials, and therefore would evaporate from stick products leading to hardening of the stick.

Other variations and modifications may be made in the compounds, compositions, and methods, described herein without departing from the essential features and concepts of the present invention. The forms of the invention described herein are exemplary only and are not intended as limitations on the scope of the invention as defined in the appended claims.

That which is claimed is:

1. In a lipcare cosmetic composition containing as ingredients thereof an emollient, a wax, a suspending agent, a coloring agent, and further including as an additional ingredient an organosilicon compound, the improvement comprising the organosilicon compound being an alkylmethylpolysiloxane having the formula

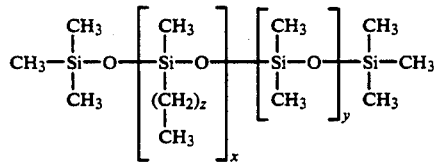

in which x has a value of 1-50; y has a value of 1-300; and z has a value of 5-50.

2. A composition according to claim 1 in which x has a value of 3-40; y has a value of 2-190; and z has a value of 5-30.

3. A composition according to claim 1 which includes from one to twenty-five percent by weight of one or more emollients; ten to twenty percent by weight of one or more waxes; 0.5 to 1.0 percent by weight of a suspending agent; three to ten percent by weight of one or more coloring agents; forty to sixty percent by weight of castor oil; one to twenty percent by weight of the alkylmethylpolysiloxane; 0.1 to 0.5 percent by weight of a preservative; and 0.05 to 0.1 percent by weight of an antioxidant.

4. A composition according to claim 3 in which the emollient selected from the group consisting of octyl dodecanol and lanolin oil.

5. A composition according to claim 3 in which the waxes selected from the group consisting of candelilla wax, ozokerite wax, and carnauba wax.

6. A composition according to claim 3 in which the coloring agent is a mixture of coloring agents in the form of a dispersion in castor oil.

7. A composition according to claim 2 in which z has a value from twelve to thirty carbon atoms.

8. A composition according to claim 7 in which z has a value from eighteen to twenty-four carbon atoms.

9. A method of enhancing the durability on lips of a lipcare cosmetic composition containing an emollient, a wax, a suspending agent, and a coloring agent, comprising applying to the lips a lipcare cosmetic composition which includes as an ingredient thereof an alkylmethylpolysiloxane having the formula

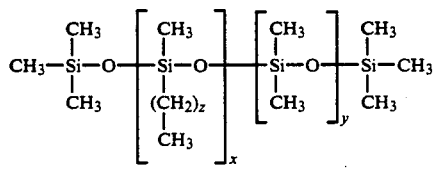

in which x has a value of 1–50; y has a value of 1–300; and z has a value of 5–50.

10. A method according to claim 9 in which x has a value of 3–40; y has a value of 2–190; and z has a value of 5–30.

11. A method according to claim 9 in which the lipcare cosmetic composition includes from one to twenty-five percent by weight of one or more emollients; ten to twenty percent by weight of one or more waxes; 0.5 to 1.0 percent by weight of a suspending agent; three to ten percent by weight of one or more coloring agents; forty to sixty percent by weight of castor oil; one to twenty percent by weight of the alkylmethylpolysiloxane; 0.1 to 0.5 percent by weight of a preservative; and 0.05 to 0.1 percent by weight of an antioxidant.

12. A method according to claim 11 in which the emollient selected from the group consisting of octyl dodecanol and lanolin oil.

13. A method according to claim 11 in which the waxes selected from the group consisting of candelilla wax, ozokerite wax, and carnauba wax.

14. A method according to claim 11 in which the coloring agent is a mixture of coloring agents in the form of a dispersion in castor oil.

15. A method according to claim 10 in which z has a value to from twelve to thirty carbon atoms.

16. A method according to claim 15 in which z has a value to from eighteen to twenty-four carbon atoms.

* * * * *